United States Patent
Duston et al.

(10) Patent No.: US 7,032,831 B2
(45) Date of Patent: Apr. 25, 2006

(54) CONTAINER FOR A DEVICE FOR DISPENSING A VOLATILE LIQUID

(75) Inventors: Tyler D. Duston, Evanston, IL (US);
Kishen Gohil, New Malden (GB);
Colin W. Brown, Egham (GB); Guy Naish, Bicester (GB); Kara L. Kotary, Racine, WI (US); Marygrace G. Horner, Racine, WI (US); Mary Beth Adams, Gurnee, IL (US); Ralph Schwarz, Racine, WI (US); Padma Prabodh Varanasi, Racine, WI (US); Ann E. Weeks, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 142 days.

(21) Appl. No.: 10/394,621

(22) Filed: Mar. 21, 2003

(65) Prior Publication Data

US 2004/0182949 A1    Sep. 23, 2004

(51) Int. Cl.
*A24F 12/14* (2006.01)

(52) U.S. Cl. ............ 239/44; 239/47; 239/51.5; 239/57; 220/694

(58) Field of Classification Search ............ 239/34, 239/44, 47, 51.5, 53, 57; 392/390, 394, 395, 392/403; 220/694, 737; 261/104, 107; 422/123, 124, 305, 306
See application file for complete search history.

(56) References Cited

U.S. PATENT DOCUMENTS

| | | | |
|---|---|---|---|
| 1,911,871 A | 5/1933 | Anderson | |
| 2,435,811 A | 2/1948 | Waters | |
| 2,557,501 A | 6/1951 | Fusay et al. | |
| 2,764,789 A | 10/1956 | Zelenka | |
| 2,828,953 A | 4/1958 | Hartmann | 261/30 |
| 3,080,624 A | 3/1963 | Weber, III | |
| 3,587,968 A | 6/1971 | Balland et al. | 239/47 |
| 3,633,881 A | 1/1972 | Yurdin | |
| 3,748,464 A | 7/1973 | Andeweg | |
| 3,749,904 A | 7/1973 | Graff | |
| 3,761,702 A | 9/1973 | Andeweg | |
| 3,790,081 A | 2/1974 | Thornton et al. | |

(Continued)

FOREIGN PATENT DOCUMENTS

AU    664685    11/1995

(Continued)

OTHER PUBLICATIONS

International Search Report and Written Opinion, Aug. 16, 2004, Appl. No. PCT/US04/008436.

(Continued)

*Primary Examiner*—Steven J. Ganey

(57) ABSTRACT

A container for a volatile liquid in a liquid dispensing device comprises a body and a neck extending from the body to define an opening. A retention structure is integral with the container body and is adapted to be releasably engaged with two opposing sidewalls of a housing of the dispensing device. The sidewalls are spaced apart in a first direction, and the retention structure is inhibits motion of the container in two opposing directions generally transverse to the first direction. The retention structure may be located on a side of the container body. A capillary member extends from inside the container to an exterior of the container. The volatile liquid migrates along the capillary member from the reservoir to the exterior of the container where it is evaporated from the surface of the capillary member by forced airflow generated by a motorized fan mounted in the housing.

31 Claims, 6 Drawing Sheets

U.S. PATENT DOCUMENTS

| | | |
|---|---|---|
| 3,890,085 A | 6/1975 | Andeweg |
| 3,923,458 A | 12/1975 | Moran |
| 3,948,445 A | 4/1976 | Andeweg |
| 3,990,848 A | 11/1976 | Corris |
| 3,993,444 A | 11/1976 | Brown |
| 4,035,451 A | 7/1977 | Tringali |
| 4,166,087 A | 8/1979 | Cline et al. |
| 4,276,236 A | 6/1981 | Sullivan et al. |
| 4,294,778 A | 10/1981 | DeLuca |
| 4,323,193 A | 4/1982 | Compton et al. |
| 4,346,059 A | 8/1982 | Spector |
| 4,383,951 A | 5/1983 | Palson |
| 4,432,938 A | 2/1984 | Meetze, Jr. |
| 4,493,011 A | 1/1985 | Spector |
| 4,621,768 A | 11/1986 | Lhoste et al. ............... 239/44 |
| 4,660,764 A | 4/1987 | Joyaux et al. ............... 239/44 |
| 4,666,638 A | 5/1987 | Baker et al. |
| 4,695,435 A | 9/1987 | Spector |
| 4,707,338 A | 11/1987 | Spector |
| 4,739,928 A | 4/1988 | O'Neil |
| 4,743,406 A | 5/1988 | Steiner et al. |
| 4,857,240 A | 8/1989 | Kearnes et al. |
| 4,866,580 A | 9/1989 | Blackerby |
| 4,913,350 A | 4/1990 | Purzycki |
| 4,928,881 A * | 5/1990 | Barlics et al. ............... 239/44 |
| 4,931,224 A | 6/1990 | Holzner, Sr. |
| 4,968,487 A | 11/1990 | Yamamoto et al. ......... 422/125 |
| RE33,864 E | 3/1992 | Steiner et al. |
| 5,095,647 A | 3/1992 | Zobele et al. |
| 5,114,625 A | 5/1992 | Gibson |
| 5,126,078 A | 6/1992 | Steiner et al. |
| 5,133,042 A | 7/1992 | Pelonis |
| 5,217,696 A | 6/1993 | Wolverton et al. |
| 5,223,182 A | 6/1993 | Steiner et al. |
| 5,342,584 A | 8/1994 | Fritz et al. |
| 5,370,829 A | 12/1994 | Kunze |
| 5,376,338 A | 12/1994 | Zlotnik |
| 5,547,616 A | 8/1996 | Dancs et al. |
| 5,647,053 A | 7/1997 | Schroeder et al. |
| 5,651,942 A | 7/1997 | Christensen |
| 5,662,835 A | 9/1997 | Collingwood |
| D386,974 S | 12/1997 | Wefler |
| D393,063 S | 3/1998 | Wefler |
| 5,891,400 A | 4/1999 | Ansari et al. |
| 5,909,845 A | 6/1999 | Greatbatch et al. |
| 5,919,423 A | 7/1999 | Requejo et al. |
| 5,970,643 A | 10/1999 | Gawel, Jr. |
| 5,980,064 A | 11/1999 | Metroyanis |
| 6,017,139 A | 1/2000 | Lederer |
| 6,104,867 A | 8/2000 | Stathakis et al. ........... 392/403 |
| 6,106,786 A | 8/2000 | Akahoshi |
| 6,196,706 B1 | 3/2001 | Cutts |
| 6,241,161 B1 | 6/2001 | Corbett |
| 6,354,710 B1 | 3/2002 | Nacouzi |
| 6,361,752 B1 | 3/2002 | Demarest et al. ........... 422/306 |
| 6,371,450 B1 | 4/2002 | Davis et al. |
| 6,454,425 B1 | 9/2002 | Lin ............... 362/96 |
| 6,484,438 B1 | 11/2002 | Matsunaga et al. ........... 362/96 |
| 6,555,068 B1 | 4/2003 | Smith |
| 6,616,308 B1 | 9/2003 | Jensen et al. ............... 362/351 |
| 6,619,560 B1 * | 9/2003 | Chun ............... 239/44 |
| 6,862,403 B1 | 3/2005 | Pedrotti et al. |
| 2002/0080601 A1 | 6/2002 | Meltzer ............... 362/96 |
| 2002/0093834 A1 | 7/2002 | Yu et al. ............... 362/565 |
| 2002/0136542 A1 | 9/2002 | He et al. ............... 392/395 |
| 2002/0136886 A1 | 9/2002 | He et al. ............... 428/313.5 |
| 2003/0007887 A1 | 1/2003 | Roumpos et al. ............... 422/1 |
| 2003/0053305 A1 | 3/2003 | Lin ............... 362/96 |
| 2003/0146292 A1 | 8/2003 | Schramm et al. |
| 2004/0141315 A1 | 7/2004 | Sherburne ............... 362/161 |
| 2004/0246711 A1 | 12/2004 | Brenchley et al. ........... 362/161 |
| 2004/0265196 A1 | 12/2004 | Varanasi et al. |

FOREIGN PATENT DOCUMENTS

| | | | |
|---|---|---|---|
| DO | DM/054926 | 9/2000 | |
| EP | 0 882 459 | 12/1998 | |
| EP | 1 031 446 | 8/2000 | |
| EP | 1 270 021 | 1/2003 | |
| EP | 1 283 062 | 2/2003 | ............... 9/3 |
| EP | 1 392 368 | 10/2003 | |
| EP | 1 283 062 A1 | 12/2003 | |
| GB | 2285579 | 7/1995 | |
| WO | WO 95/10352 | 4/1995 | |
| WO | WO 01/02025 A1 | 1/2001 | |
| WO | WO 01/23008 A1 | 4/2001 | |
| WO | WO 02/30220 A1 | 4/2002 | |
| WO | WO 02/31413 A2 | 4/2002 | |
| WO | WO 03/013618 | 2/2003 | |
| WO | WO03/086487 | 10/2003 | |
| WO | WO 2004/030708 | 4/2004 | |

OTHER PUBLICATIONS

International Search Report and Written Opinion, Aug. 16, 2004, Appl. No. PCT/US04/008437.

"Inglow™Candle Company" www.inglowcandle.com (2002).

"Luna Candles" http://www.epartyunlimited.com/luna-candles.html (print date 2005).

* cited by examiner

CONTAINER FOR A DEVICE FOR DISPENSING A VOLATILE LIQUID

FIELD OF THE INVENTION

The present invention relates to emanation systems for volatile liquids and, more particularly, to a container for a volatile liquid in a liquid dispensing device.

DETAILED DESCRIPTION OF THE INVENTION

Figure 1:
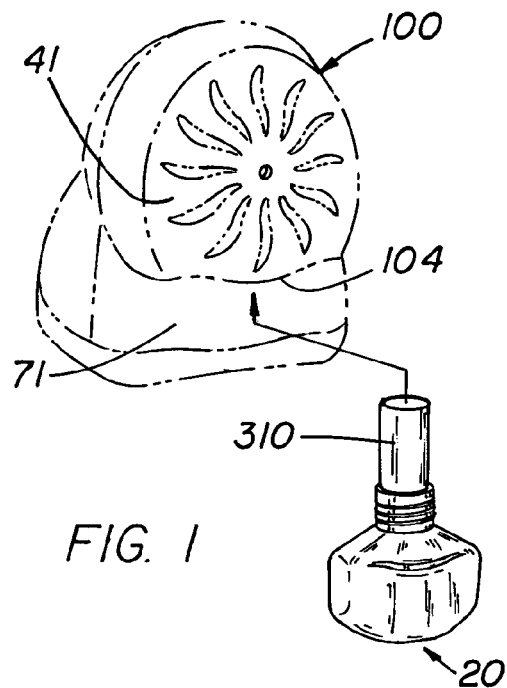
FIG. 1 is a perspective view showing insertion of the container of the present invention into a housing of a dispensing device.

Referring to FIG. 1, container 20 of the present invention is releasably secured to a housing 100 of a dispenser for a volatile liquid, such as a fragrance compound. Container 20 serves as a reservoir for the volatile liquid. A capillary member 310 is secured in an opening of container 20. A portion of capillary member 310 extends into an interior of container 20 to contact the volatile liquid. Another portion of capillary member 310 extends outside container 20. When container 20 is secured in housing 100, a portion of the container and the portion of capillary member 310 extending outside container 20 resides in an interior of housing 100. The volatile liquid migrates along capillary member 310 from the reservoir to the exterior of container 20 where it is evaporated from an exterior surface of capillary member 310 by forced airflow generated by a motorized fan mounted in housing 100. In this instance, container 20 is secured in a position on housing 100 such that the portion of capillary member 310 residing in the interior of housing 100 resides in the forced air stream generated by the fan.

Referring to FIGS. 1, 1A, 2 and 3, container 20 of the present invention is configured to be inserted into an opening 104 in housing 20. Container 20 includes a body 22, a neck 23 extending from the body and defining an opening 24 for receiving the volatile liquid therethrough, a pair of opposing sides 26, 28 on opposite sides of the opening, and a pair of sidewalls 30, 32, each sidewall intersecting each of opposing sides 26, 28 at ends thereof. Straight surfaces 34, 36 may be formed in one or both of sidewalls 30, 32 to aid a user in grasping the container during extraction of the container from the housing.

Figure 6:
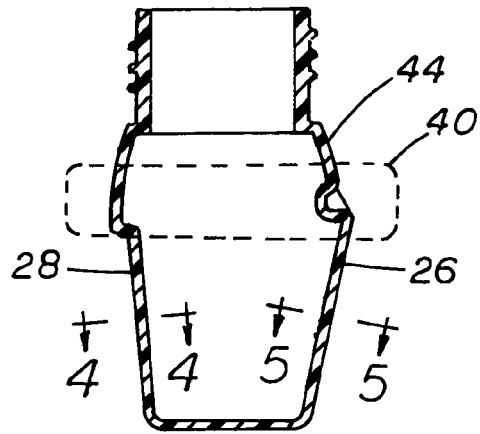
FIG. 6 is a longitudinal cross-sectional view of the container of FIG. 1.
Figure 7:
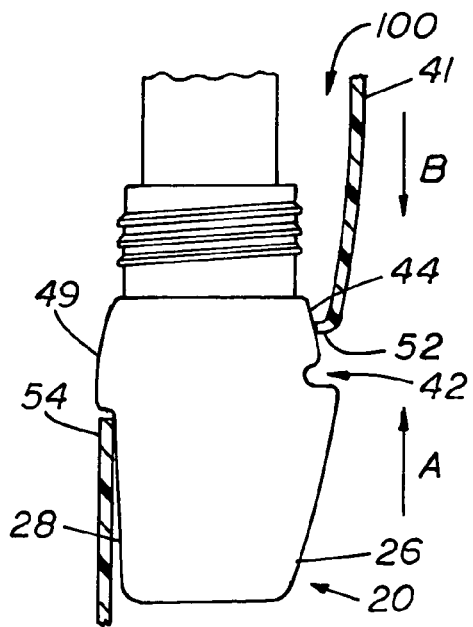
FIG. 7 is an end view of the container of FIG. 1 during insertion into the housing with the housing partially cut away.
Figure 8:
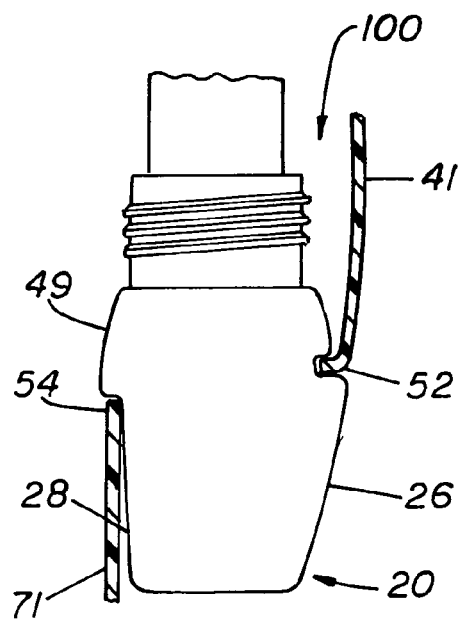
FIG. 8 is an end view of the container of FIG. 1 fully inserted into the housing with the housing partially cut away.

Referring to FIGS. 3–8, it may be seen that opposing sides 26, 28 each have a concave curvature with respect to an interior 180 of the container. The curvature of side 28 may substantially conform to a complementary surface 38 of housing 100, to aid in the securement and positioning the container with respect to the housing. Also, as seen in FIG. 8, side 26 of container 20 may be configured to align with a contour of an adjacent surface 40 of the housing when container 20 is secured in housing 100 which aids in maintenance of the securement of the container.

Figure 4:
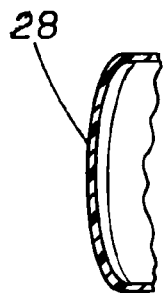
FIG. 4 is a cross-sectional view along line 4—4 of a side of the container as shown in FIG. 6.
Figure 5:
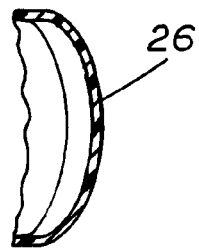
FIG. 5 is a cross-sectional view along line 5—5 of another side of the container as shown in FIG. 6.

FIG. 4 is a cross-sectional view of container side 28, and FIG. 5 is a cross-sectional view of container side 26. Referring to FIGS. 4–6, it may be seen that side 28 has a radius of curvature R1 greater than a radius of curvature R2 of side 26. Also, as seen in FIG. 6, side 26 is angled with respect to side 28. Defining an axis of curvature of a given curved surface as a line that is equidistant from all points along the curved surface, it is also seen that, as a result of the angled relationship between sides 26 and 28, an axis of curvature of side 26 has a corresponding angled relationship with axis of curvature of side 28. This orientation of sides 26 and 28 likewise facilitates the maintenance of securement of the container to the housing.

Figure 1A:
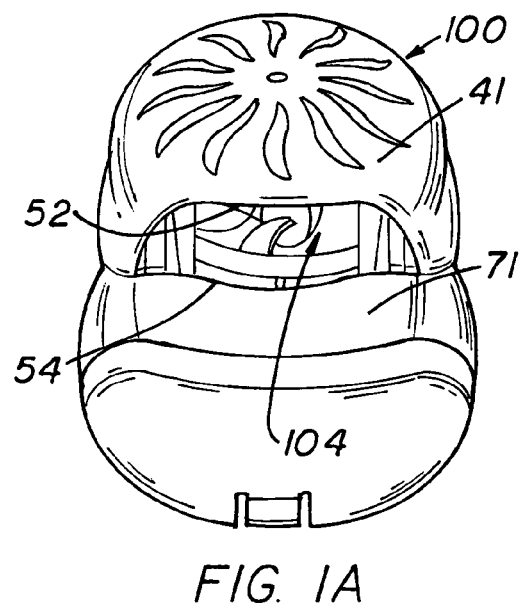
FIG. 1A is a perspective view of the housing of FIG. 1 showing the opening into which the container is inserted.
Figure 2:
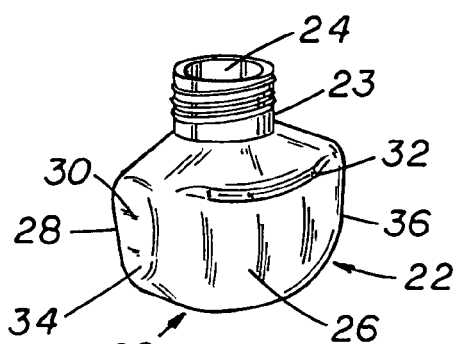
FIG. 2 is a perspective view of the container of FIG. 1.
Figure 3:
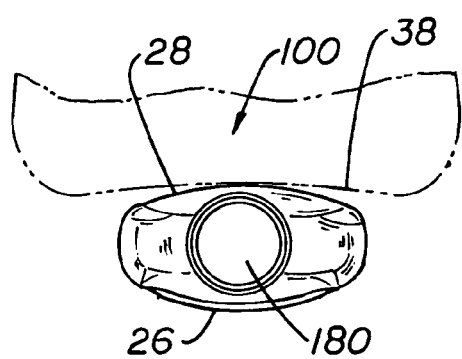
FIG. 3 is a top plan view of the container of FIG. 1.

Referring to FIGS. 1A, 2, 6, 6A and 7, each of opposing sidewalls 41 and 71 has a corresponding edge portion 52, 54. Edge portions 52, 54 define an opening 104, as seen in FIG. 1A, adapted to receive a portion of container 20 therein. In the embodiments described herein, a portion of container 20 resides in an interior of housing 100 when container 20 is secured in its desired position on the housing. A retention structure, generally designated 40, as seen in FIG. 6, is formed along one or more of opposing sides 26, 28 to position and releasably secure container 20 between two opposing sidewalls 41, 71 of housing 100. Retention structure 40 may be formed integral with container 20. Alternatively, retention structure 40 may be incorporated into one or more components separate from container 20 and designed to be affixed to container 20.

In a manner described below, retention structure is adapted to engage the edge portion of at least one of the two opposing housing sidewalls 41 and 71 to inhibit motion of the container in two opposing directions, as demonstrated by arrows A and B shown in FIG. 7, relative to the housing.

Figure 6A:
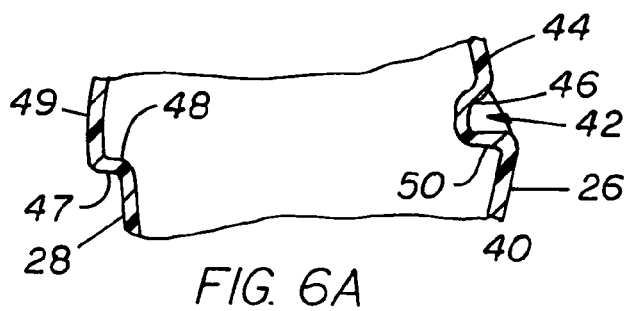
FIG. 6A is an enlarged view of the cross-sectional view in FIG. 6 designated by enclosure 40.

FIG. 6A shows a magnified view of retention structure 40. Referring to FIGS. 6 and 6A, in a first embodiment retention structure 40 includes a recess 42 formed in surface 26 of container 20 and adapted to receive edge portion 52 of housing sidewall 26 therein as seen in FIGS. 7 and 8. An inclined surface 44 may be formed on surface 26 of container 20 adjacent recess 42. In general, the inclined surfaces described in this embodiment and in the following alternative embodiments serve as ramps for the purpose of slidingly engaging an edge of the housing during insertion of the container into the interior portion of the housing, thereby easing insertion of the container into the housing interior. Inclined surface 44 may either be slightly curved or substantially straight. Recess 42 has a slightly sloped inner surface 46 extending along a side of thereof opposite inclined surface 44. Recess 42 also has an inner surface 50 formed opposite sloped inner surface 46.

In addition to recess 42 formed on surface 26 of the container, a projection 48, as seen in FIG. 6A, and an adjacent inclined surface 49 are formed on surface 28 of container 20 for engaging a second edge portion 54 of housing 20 different from first edge portion 52 described above. As shown, projection 48 is formed on a container surface 28 which is opposite, and spaced apart from, container surface 26 on which recess 42 is formed. A side of projection 48 opposite the side on which inclined surface 49 is formed may include a slightly sloped surface 47 for slidingly engaging second edge portion 54 during extraction of container 20 from housing 100.

Engagement and disengagement of retention structure 40 with housing 100 will now be described.

In a first embodiment, as seen in FIGS. 1A, 6–8, retention structure 40 engages a first edge portion 52 and a second edge portion 54 upon insertion to position and releasably secure container 20 in housing 100. In the embodiment shown, first edge portion 52 extends generally transversely toward second edge portion 54.

Figure 9:
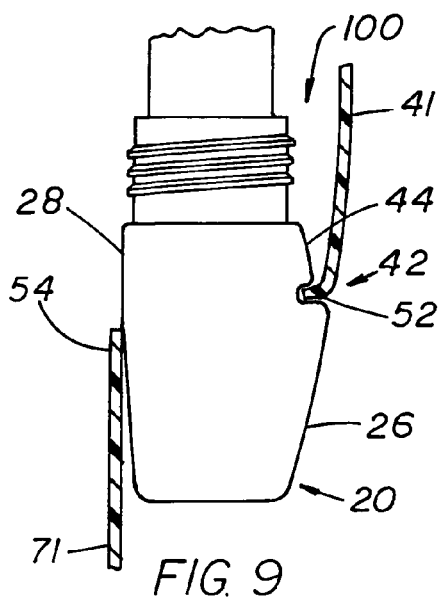
FIGS. 9–12 are end views of alternative embodiments of the container of FIG. 1 fully inserted into the housing with the housing partially cut away.

Referring to FIGS. 6, 6A, 7 and 8, when container 20 is moved toward housing 100 in the direction indicated by arrow "A", inclined surface 44 engages edge portion 52 and slides along edge portion 52. Edge portion 52 and/or inclined surface 44 may resiliently deflect during sliding of inclined surface 44 along edge portion 52. Similarly, edge portion 54 slides along inclined surface 49 adjacent projection 48. Referring to FIG. 9, sliding engagement between inclined surface 44 and edge portion 52 continues until container 20 reaches a position where edge portion 52 enters recess 42, wherein edge portion 52 returns to a substantially undeflected state, thereby securing container 20 between edge portions 52 and 54. Also, at this time, edge portion 54 slides over an intersection between inclined surface 49 and sloped surface 47 engages edge portion 54, returning to a substantially undeflected state.

From the above description, it may be seen that when container 20 is releasably secured in housing 100, retention structure 40 described above (FIG. 6 and 6A) will effectively inhibit motion of container 20 in the two opposing directions "A" and "B" relative to the housing. Specifically, referring to FIGS. 6A and 8, engagement between recess inner surface 50 and edge portion 52 will inhibit motion of container 20 in the direction indicated by arrow "A" to aid in preventing over-insertion of container 20 into the housing interior. In addition, engagement between recess sloped inner surface 46 and edge portion 52 will inhibit motion of container 20 in the direction indicated by arrow "B", to inhibit extraction of container 20 from the housing interior. Finally, engagement between projection sloped surface 47 and second edge portion 54 during extraction of the container aids in inhibiting extraction of the container from the housing.

Referring again to FIGS. 6, 6A and 8, when container 20 is to be disengaged from housing 100, container 20 is grasped along straight surfaces 34, 36 (FIGS. 2 and 3) and pulled in the direction indicated by arrow "B". Recess sloped surface 46 then acts as a detent, slidingly engaging edge portion 52 and moving along edge portion 52 in the direction indicated by arrow "A" until edge portion 52 reaches an intersection of sloped surface 46 with inclined surface 44. Edge portion 52 then slides along inclined surface 44 until container 20 is disengaged from edge portion 52. Similarly, edge portion 54 slides along sloped surface 47 until edge portion 54 reaches an intersection of sloped surface 47 with inclined surface 49. Edge portion 54 then slides along inclined surface 49 until container 20 is disengaged from edge portion 54.

Referring to FIG. 9, another embodiment of the retention structure incorporates only recess 42 formed in container side 26. Projection 48 is not formed on opposing container side 28. Operation of the retention structure during insertion and withdrawal of the container is as described for the first embodiment.

Figure 10:
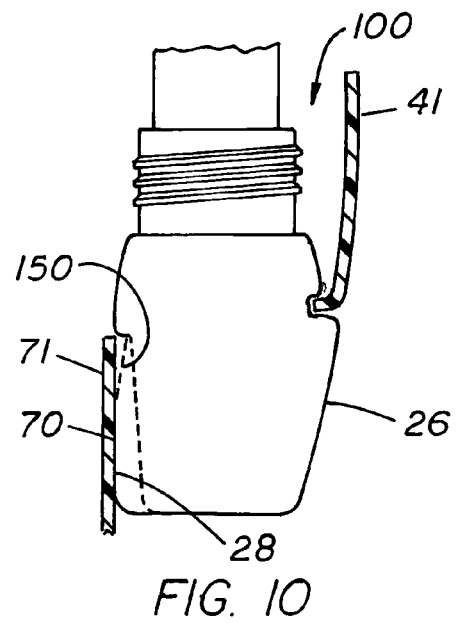

In another embodiment, shown in FIG. 10, the retention structure may be in the form of an adhesive adapted to adhere the container to a surface of the housing. The adhesive may be applied directly to a surface 28 of the container and/or a corresponding surface 70 of the housing. Alternatively, the adhesive may be in the form of an adhesive tape, for example, a double-sided tape applied to one of the container surface or the corresponding housing surface.

Additional alternative embodiments of the retention structure are also contemplated which will position and releasably secure the container to housing 100. For example, referring to FIG. 10, an inclined surface 150 may be formed along housing surface 70, rather than along side 28 of the container, for slidingly engaging side 28 during mounting of the container on the housing.

In another embodiment (not shown), the retention structure may also be in the form of a latching member formed integral with the container and adapted to engage a complementary latch-receiving feature on the housing. Alternatively, the container may have a latch-receiving feature formed thereon for engaging a complementary latching member formed on the housing.

Figure 11:
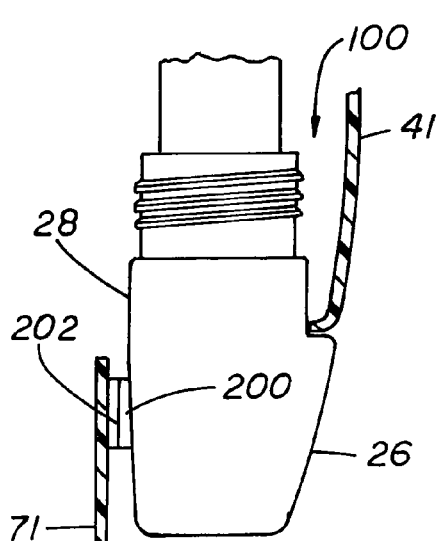

Referring to FIG. 11, in yet another embodiment, the retention structure may be in the form of a releasable mating hook-and-loop type fastening member 200 adapted to mate with a complementary fastening member 202 positioned on the housing.

Figure 12:
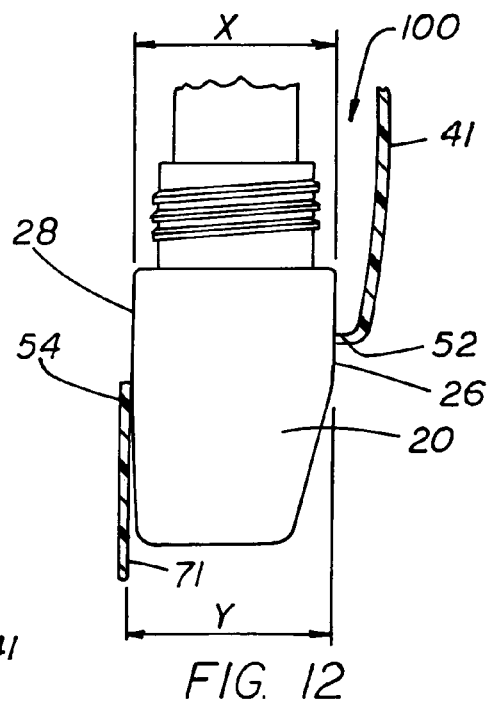

Referring to FIG. 12, the retention structure may alternatively be formed by opposing sides 26, 28 of the container dimensioned so as to form an create an interference fit between container 20 housing 100. For example, dimension "X" extending across opposing container surfaces 26, 28 may be made slightly larger than a distance "Y" separating spaced apart first and second housing portions 52, 54. Thus, when container 20 is inserted into housing 100, an interference fit is generated between opposing container surfaces 26, 28 and first and second housing portions 52, 54.

From the above descriptions, it may be seen that when container 20 is releasably secured in housing 100, any of the alternative retention structure embodiments described above will effectively inhibit motion of the container in the two opposing directions "A" and "B" relative to the housing.

Figure 13:
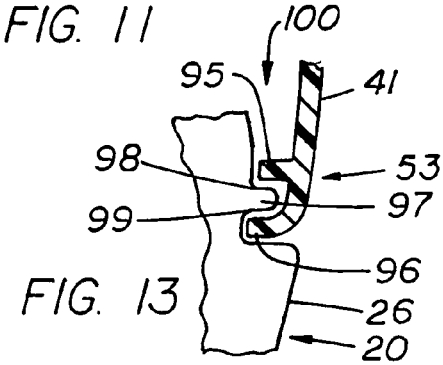
FIG. 13 is an enlarged view of a retention structure formed on the container of FIG. 1 with the container partially cut away.

Referring to FIG. 13, in another embodiment of the retention structure a projection 97 is formed along side 26 of the container in a position to engage a housing edge portion 53 when container 20 is inserted into housing 100. A pair of inclined surfaces 98, 99 is formed on side 26 adjacent projection 97 on either side of the projection for slidingly engaging a housing edge portion 53 during insertion and extraction of container 20 from housing 100, in the manner described above. In this embodiment, edge portion 53 includes a pair of edge walls 95, 96 projecting in a direction generally transverse to the insertion direction of container 20 into housing 100. Edge walls 95, 96 form a recess for receiving projection 97 therein to releasably secure container 20 to housing 100.

Referring to FIGS. 1 and 14–17, a capillary member 310 is to be secured in opening 24 (FIG. 2) of container 20. One portion 310*a* (FIG. 15) of capillary member 310 extends into the interior 180 of container 20 to contact the volatile liquid. Another portion 310*b* (FIG. 15) of capillary member 310 extends outside container 20. When the container is secured in housing 100, a portion of container 20 and the portion 310*b* of capillary member extending outside container 20, resides in an interior of the housing. The volatile liquid migrates along capillary member 310 from the reservoir to the exterior of container 20 where it is evaporated from the surface of capillary member 310 by forced airflow generated by a motorized fan mounted in housing 100. In one form, capillary member 310 secured in container 20 is in the form of a wick and, for illustrative purposes, the terms "capillary member" and "wick" will be used synonymously hereinafter. Detailed descriptions of some representative wick structures which may be secured in the container of the present invention are provided in co-pending patent applications having U.S. Ser. Nos. 10/266,512; 10/266,798; and 10/266,546 and are incorporated herein by reference.

Figure 14:
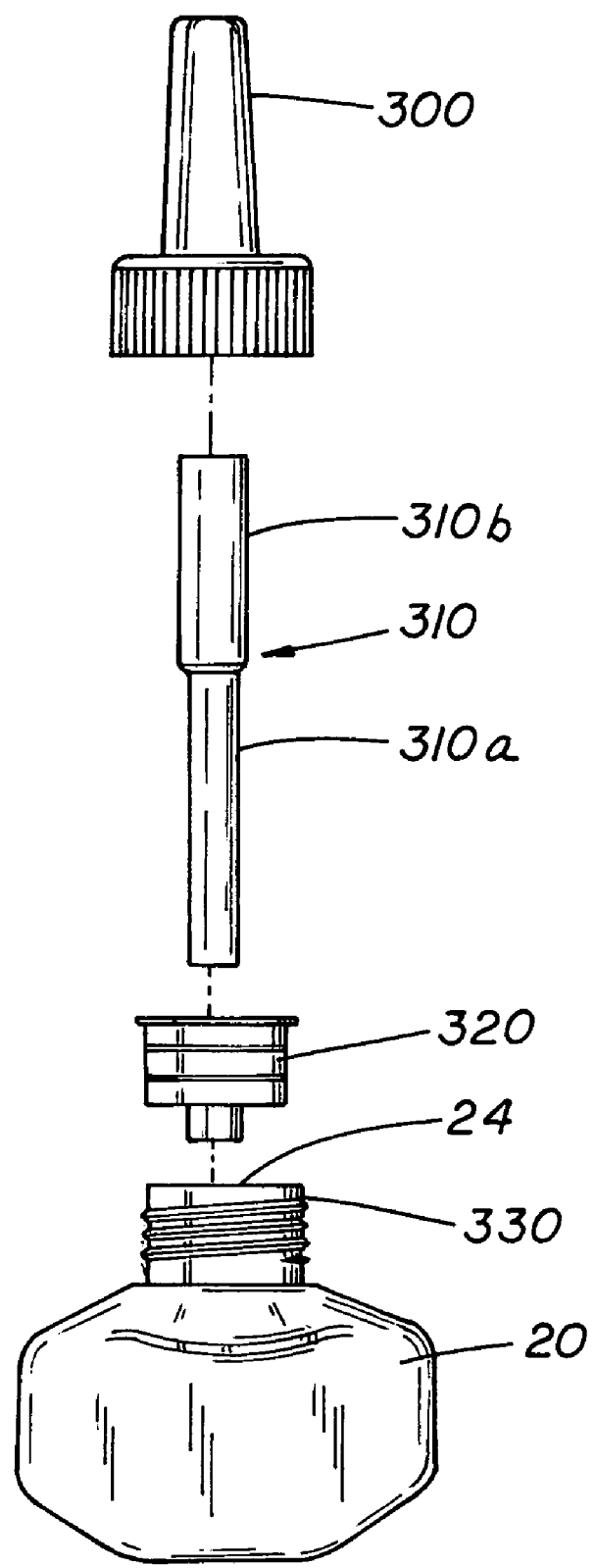
FIG. 14 is an exploded view of a wick secured in the container of FIG. 1.

Referring to FIG. 14, a portion of wick 310 that is co-extensive with neck 330 of container 20 is shaped so that it fits snugly into the neck 330 of the container 20. The wick 310 is long enough so that its bottom surfaces come into contact with the liquid in the container 20 and its top surfaces are exposed to the ambient air. (The level of the liquid is not shown in the container 20.) It is preferable to use a neck closure 320, such as that shown in FIG. 14, to hold the wick 310 in place and to prevent leakage around the neck 330 of the container 20. The fit between the neck closure 320 and the container 20 is tight enough to prevent leakage of the liquid from the container 20. Likewise, the fit between the neck closure 320 and the wick 310 is sufficiently tight to prevent leakage of the liquid from the container 20.

In addition, the neck 330 of the container 20 may be shaped so that a cover 300 can be securely fastened over the wick 310 and neck closure 320. For example, the outer neck 330 of the container 20 may be threaded so that cover 330 can be screwed on top of the container 20 when the device is not in use.

Referring again to FIG. 14, the container 20 and the neck closure 320 can be made of any suitable material that is leakproof and adaptable to incorporate the characteristics of the retention structure embodiments described herein. The size of the opening in the container 20 and the size of the neck closure 320 are dependent upon each other and upon the size of the wick 310 that is to be used with the device.

The neck closure 320 or neck 330 of the container 20 may be formed with a small hole (e.g., a vent-hole) to help counter the effects of a vacuum that can form in the head-space of the container 20. The wick 310 transports the liquid to the surface of the wick 310 by a principle called capillary action. In particular, the wick material contains numerous pores, and these pores act as capillaries, which cause the liquid to be drawn into them. As the liquid is drawn from the container and transported up the porous wick 310, a vacuum is created in the head-space of the container 20.

The formation of a vacuum in the head-space of the container 20 decreases the rate that the liquid is wicked from the reservoir to the surface. This decrease in the wicking rate translates directly into a decrease in the release rate of the liquid to the ambient air. Accordingly, in order to combat the formation of the vacuum in the head-space, it is often preferable to form a vent-hole in the vicinity of the head-space of the container 20. However, if the container 20 is overturned, either during shipping or, later, during handling of the bottle by the consumer, it is possible for the concentrated liquid in the container 20 to leak out of the vent-hole. Therefore, if is preferable to design a device that does not require a vent-hole.

It has been found that if the pore size of the wick 310 is below a critical size, the vent-hole can be eliminated without sacrificing the release rate of the vaporizable liquid into the ambient air. Because the capillary force increases as the pore size of the wick 310 decreases, a wick 310 with very small porosity has a very strong capillary force. This strong capillary force allows the wick 310 to continue to be able to transport the liquid from the container 20 to the surface of the wick 310 even though a vacuum has formed in the head-space of the container 20. In other words, a wick 310 with a very small pore size is able to overcome the vacuum effect that is present in the head-space of the container 20.

The critical size of the wick 310 is determined by the surface tension of the liquid, the compatibility of the wick 310 and liquid (i.e., the contact angle), and the extent to which a vacuum is generated with the head-space of the container 20. In particular, we have found that if the wick 310 is manufactured with a mean pore size that is below about four microns, the effects of a vacuum in the head-space of the container 20 can be greatly decreased. Specifically, we have found that it is most preferable that the mean pore size of the wick 310 be below about one micron. When the wick 310 has a mean pore size of below four microns, and preferably below one micron, we have found that the wick 310 is still able to effectively function to transport the liquid from the container 20 to the surface of the wick 310.

When using a device of this invention, it is not necessary to provide a vent-hole in the upper part of the container 20, or in the neck closure 320 because the vacuum effects are substantially decreased. By eliminating the vent-hole, the problem of spillage or leakage that occurs as a result of the existence of the vent-hole is also eliminated.

The mean pore size of the wick 310 can be determined by any standard test for determining porosity and pore size distribution. For example, mercury porosimetry is a method that gives information on porosity and pore size distribution for rigid wicks. It is based on the measurement of differential increments in the amount of mercury intruded into the wick 310 as a function of increasing applied pressure.

It has also been found that another advantage in using a wick 310 with a mean porosity of below about four microns, and preferably below about one micron, is that the lower porosity decreases the likelihood of the liquid spilling or leaking through the wick 310 itself. Since the upper surface of the wick 310 is exposed to the ambient air, if the container 20 is overturned, it is possible for liquid to leak out through a wick of conventional pore sizes. Using a smaller porosity wick 310 of this invention, however, decreases the ability of the liquid to travel through the wick 310 when the container 20 is overturned.

The wick 310 can be made of a variety of materials. It is preferable that the wick 310 be rigid enough to provide minimal contact area with the surface that the wick 310 comes in contact with. Polymeric wicks, for example, have been found to be effective for these purposes. In particular, wicks composed of ultra high molecular weight, high density polyethylene (HDPE) have been found to be suitable. Such wicks are generally comprised of blends of HDPE in particle form, and the blends are developed to meet the target pore characteristics of the wick 310.

Preferably, the solubility parameter of the polymer used in the wick 310 is significantly different from that of any of the components contained in the liquid. This prevents the wick 310 from swelling (or other changes) that may lead to a change in the pore size and porosity of the wick 310, which would consequently affect the release rate of the vaporizable liquid into the ambient air.

The wick 310 can also be made in a variety of shapes. FIG. 14, for example, shows a cylindrical wick 310 with a narrower lower region. This change in shape of the wick 310 is not required. Instead, this variation in shape can be useful in that it both increases the amount of the surface area of the wick 310 that is exposed to the ambient air and aids in forming a tighter seal at the neck 330 area of the container 20, thus helping to prevent spilling or leaking of the liquid from the container 20. The above-described benefits of using a wick 310 with a mean pore size of below about four microns, and preferably below about one micron, can be obtained with wicks of many different shapes.

Figure 15:
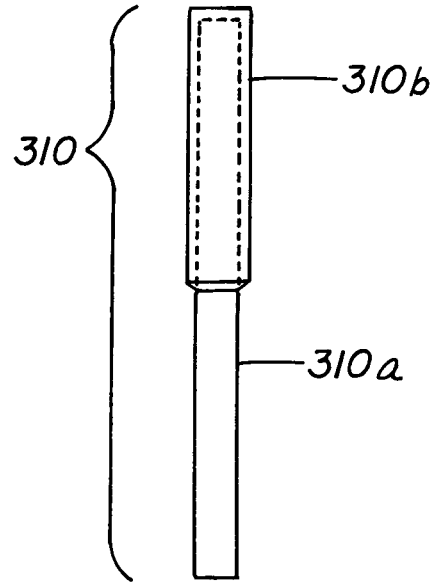
FIG. 15 is a side elevational view of one embodiment of a wick to be secured in the container of FIG. 1.
Figure 15A:
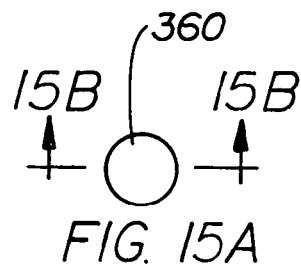
FIG. 15A is an top view of the embodiment shown in FIG. 15.
Figure 15B:
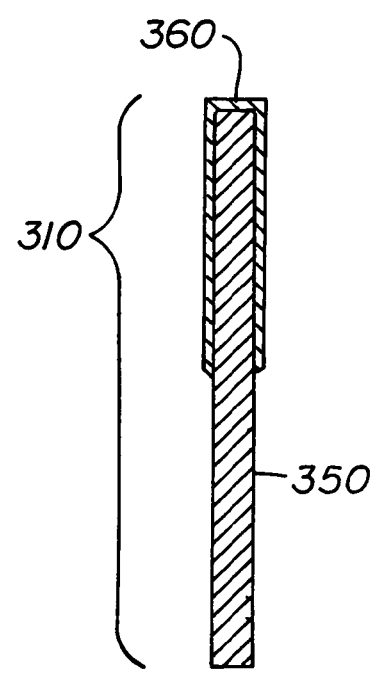
FIG. 15B is a cross sectional view along line B—B in FIG. 15A.
Figure 16A:
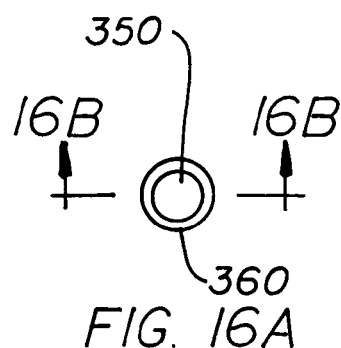
FIG. 16A is a top view of another embodiment of a wick to be secured in the container of FIG. 1.
Figure 16B:
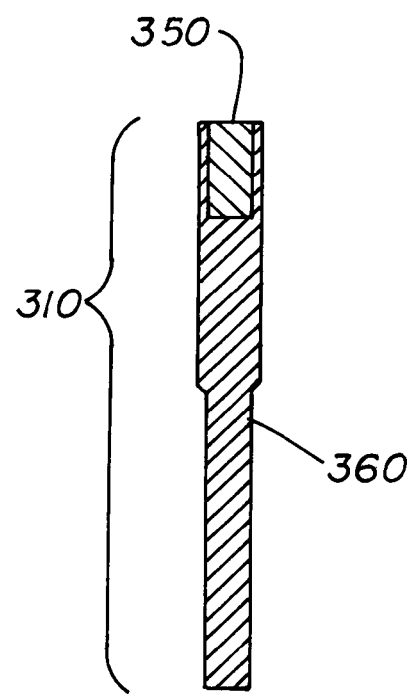
FIG. 16B is a cross sectional view along line A—A in FIG. 16A.
Figure 17A:
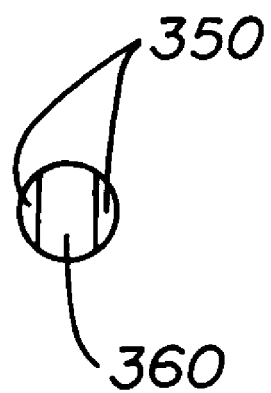
FIG. 17A is a top view of still another embodiment of a wick to be secured in the container of FIG. 1.
Figure 17B:
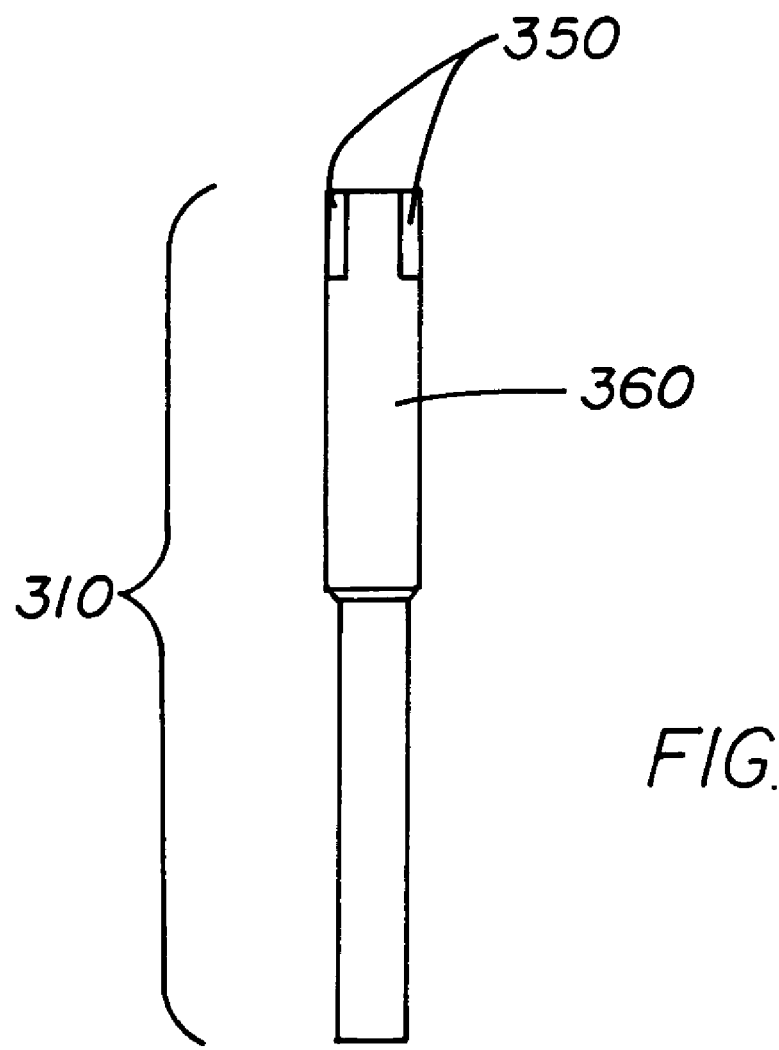
FIG. 17B is a side view of the wick of FIG. 17A.

As shown in FIG. 15, it is also possible to provide a wick 310 with an outer layer that is made up of a material with larger pore sizes. In FIG. 15, the large pore outer section 310b completely surrounds the exposed portion of the wick 310a. The small pore size section 310a extends into the container 20 and is in contact with the liquid. In this manner, the smaller pores of the inner portion 310a of the wick 310 allow the delivery system to be constructed without a vent-hole, while the larger pores of the outer portion 310b provide a maximum release rate of the vaporizable liquid off the surface of the wick 310 that is exposed to the ambient air. It should be noted, however, that the large pore section 310b need not completely surround the upper region of the small pore section 310a as shown in FIG. 15 in order to provide the benefits of this invention.

It is often desired that the volatile liquid dispenser described herein exhibit an initial spike in the release rate of the volatile liquid when the device is first activated. For example, when a fragrance dispensing device is activated, an initial spike in the release rate of the volatile liquid fragrance compound is desired in order to quickly disperse into the air a sufficient amount of the fragrance compound to effectively decrease the number of insects in the surrounding area. Once an optimum level of fragrance compound is present in the ambient air of the operating area, however, the release rate of the fragrance compound should be decreased to an amount that is sufficient to maintain that optimum level. By having two sections of varying pore size exposed to the ambient air at the same time, it is possible to achieve an initial spike effect.

Referring to FIGS. 15A, 15B, 16A, 16B, 17A and 17B, in various embodiments of the wick, the initial spike effect described above may be achieved by having a wick 310 that is comprised of at least two sections. A first section 350 is made of a material that has a predetermined pore size, while the second section 360 is made of a material that has a pore size that is greater than that of the material of the first section. Both sections of the wick are exposed to the ambient air.

In the wick embodiments described above, the cylindrical shape of the large pore section 360 is also narrowed at its lower portion. The pore size of the lower portion of large pore section 360, however, does not change with this change in diameter. Importantly, this change in shape is not required for achieving the initial spike effect. Instead, this variation in shape can be useful in that it both increases the amount of the surface area exposed to the ambient air and aids in forming a tighter seal at the neck 330 area of the container 20 (FIG. 14), thus helping to prevent spilling or leaking of the liquid from the container 20.

In the above-described embodiments, the wick is longitudinal, has a longitudinal axis and a curved exterior surface. In alternative embodiments, the wick may be formed such that a cross-section of the wick taken perpendicular to the longitudinal axis has any one of a variety of simple geometric shapes, such as a circle, a diamond, a rectangle, a hexagon, an octagon, an oval or a triangle.

INDUSTRIAL APPLICABILITY

The container of the present invention is releasably secured to a housing of a unit for dispensing a volatile substance, such as a fragrance compound. Thus, the container can serve as a disposable reservoir for the volatile substance. In addition, the structure of the container serves to position a portion of a capillary member in the path of an airflow generated by a fan mounted in the housing. This positioning of the capillary member within a forced airflow ensures rapid and efficient dissemination of a volatile substance drawn through the capillary member from the reservoir.

It should be understood that the preceding is merely a detailed description of various embodiments of this invention and that numerous changes to the disclosed embodiment can be made in accordance with the disclosure herein without departing from the spirit or scope of the invention. The preceding description, therefore, is not meant to limit the scope of the invention. Rather, the scope of the invention is to be determined only by the appended claims and their equivalents.

What is claimed is:

1. A container comprising:
   a body;
   a neck extending from the body defining an opening; and
   a retention structure integral with the body, adapted to be positioned between two opposing sidewalls of a housing of a dispenser for a volatile liquid, in which the sidewalls are spaced apart in a first direction, in which the two opposing sidewalls each have an edge portion in which the edge portions define an opening adapted to receive the neck into an interior of the housing, and the retention structure being adapted to engage the edge portion of at least one of the two opposing sidewalls to inhibit motion of the container in two opposing directions relative to the housing and generally transverse to the first direction;
   wherein the retention structure comprises a recess formed in a surface of the body adapted to receive the edge portion of one of the two opposing sidewalls and a projection formed in an opposite surface of the body to the surface carrying the recess.

2. The container of claim 1 wherein the body has a width that is larger than a depth between the two opposite surfaces.

3. The container of claim 1 wherein the projection further includes an inclined surface formed on the surface of the body adjacent the projection.

4. The container of claim 2 wherein the recess includes an inclined surface formed on the surface of the body adjacent to the recess.

5. The container of claim 1 in which the retention structure is adapted to engage the edge portion of one of the sidewalls wherein the edge portion extends in a direction generally transverse to the two opposing directions.

6. The container of claim 1 including a capillary member positioned to extend through the opening of the container in which a portion of the capillary member extends within the container and another portion extends outside of the container.

7. The container of claim 6 in which the capillary member includes a first and second section.

8. The container of claim 7 wherein the first section is formed on top of the second section.

9. The container of claim 7 wherein each of the first section and the second section is cylindrical in shape.

10. The container of claim 6 wherein the capillary member has a curved exterior surface.

11. The container of claim 6 wherein the capillary member is elongate.

12. The container of claim 11 wherein a cross section of the capillary member taken perpendicular to a length of the member has a simple geometrical shape.

13. The container of claim 12 wherein the shape is one of a circle, a diamond, a rectangle, a hexagon, an octagon, an oval and a triangle.

14. The container of claim 1 wherein a wall forming the body of the container provides a substantially straight surface.

15. A container comprising:
a body;
a neck extending from a top of the body and defining an opening, wherein the body is adapted to be positioned between two opposing sidewalls of a housing of a dispenser for volatile liquid, the two opposing sidewalls being spaced apart in a first direction, the two opposing sidewalls each having an edge portion, the edge portions defining an opening adapted to receive the neck into an interior of the housing; and
a retention structure associated with a side of the body to engage at least one of the two opposing sidewalls to inhibit motion of the container in two opposing directions generally transverse to the first direction, wherein the retention structure comprises a recess formed in a surface of the body adapted to receive the edge portion of one of the two opposing sidewalls and a projection formed in an opposite surface of the body to the surface carrying the recess.

16. The container of claim 15 in which the retention structure is integral with the container.

17. The container of claim 15 wherein the body has a width that is larger than a depth between the two opposite surfaces.

18. The container of claim 15 wherein the retention structure further includes an inclined surface formed on the surface of the body adjacent the projection.

19. The container of claim 16 wherein the recess includes another inclined surface formed on a surface of the body adjacent the recess.

20. The container of claim 15 in which the retention structure is adapted to engage the edge portion of one of the sidewalls wherein the edge portion extends in another direction generally transverse to the two opposing directions.

21. The container of claim 15 wherein a portion of a side of the body is adapted to be positioned in an interior of the housing.

22. The container of claim 15 wherein the retention structure comprises opposing sides of the container spaced apart such that a separation distance between the opposing sides of the container is greater than another separation distance between edge portions of the two opposing sidewalls which receive the opposing sides of the container.

23. The container of claim 15 including a capillary member positioned to extend through the opening of the container in which a portion of the capillary member extends within the container and another portion extends outside of the container.

24. The container of claim 23 in which the capillary member includes a first and second section.

25. The container of claim 24 wherein the first section is formed on top of the second section.

26. The container of claim 24 wherein each of the first section and the second section is cylindrical in shape.

27. The container of claim 23 wherein the capillary member has a curved exterior surface.

28. The container of claim 23 wherein the capillary member is elongate.

29. The container of claim 28 wherein a cross section of the capillary member taken perpendicular to a length of the member has a simple geometrical shape.

30. The container of claim 29 wherein the shape is one of a circle, a diamond, a rectangle, a hexagon, an octagon, an oval and a triangle.

31. The container of claim 15 wherein a wall forming the body of the container provides a substantially straight surface.

* * * * *